(12) United States Patent
Prado et al.

(10) Patent No.: US 11,896,392 B2
(45) Date of Patent: Feb. 13, 2024

(54) SYSTEMS AND METHODS FOR NON-INVASIVE FAT COMPOSITION MEASUREMENT IN AN ORGAN

(71) Applicant: Livivos Inc., San Diego, CA (US)

(72) Inventors: Pablo Jose Prado, San Diego, CA (US); Alejandro Bussandri, San Diego, CA (US)

(73) Assignee: Livivos Inc., San Diego, CA (US)

( * ) Notice: Subject to any disclaimer, the term of this patent is extended or adjusted under 35 U.S.C. 154(b) by 14 days.

(21) Appl. No.: 17/692,002

(22) Filed: Mar. 10, 2022

(65) Prior Publication Data

US 2022/0287635 A1 Sep. 15, 2022

Related U.S. Application Data

(60) Provisional application No. 63/159,346, filed on Mar. 10, 2021.

(51) Int. Cl.
*A61B 5/00* (2006.01)
*A61B 5/055* (2006.01)
*G01R 33/48* (2006.01)

(52) U.S. Cl.
CPC .......... *A61B 5/4872* (2013.01); *A61B 5/055* (2013.01); *G01R 33/4828* (2013.01)

(58) Field of Classification Search
CPC .... A61B 5/4872; A61B 5/055; G01R 33/4828
See application file for complete search history.

(56) References Cited

U.S. PATENT DOCUMENTS

| 8,148,979 B1* | 4/2012 | Du | G01R 33/5602 324/307 |
| 2004/0024309 A1* | 2/2004 | Ferre | A61B 5/064 600/424 |
| 2004/0164736 A1* | 8/2004 | Guthausen | G01N 24/08 324/309 |

(Continued)

OTHER PUBLICATIONS

International Search Report and Written Opinion for Application No. PCT/US2022/019817, dated Jul. 21, 2022, 27 pages.

(Continued)

*Primary Examiner* — Dixomara Vargas
(74) *Attorney, Agent, or Firm* — Sheppard Mullin Richter & Hampton LLP (57) ABSTRACT

Systems and methods are provided for determine the fat composition in an organ of interest using a non-invasive health measurement system. The non-invasive health measurement system may include an open magnet NMR apparatus. The NMR apparatus may measure NMR signals in a sensitive volume of a patient. The sensitive volume may coincide with an organ of interest, such as a liver. Systems and methods disclosed herein may provide for separation of the water contribution and the fat contribution to the measured NMR signal. Diffusion based separation, $T_2$ based separation, and $T_1$ based separation may each serve as different methods for separating the water and fat contributions to the signal. Separating the water and fat contributions to the single may allow for computation of a proton density fat fraction which may reflect the fat composition of the organ of interest.

20 Claims, 7 Drawing Sheets

(56) References Cited

U.S. PATENT DOCUMENTS

| | | | |
|---|---|---|---|
| 2009/0261823 A1* | 10/2009 | Yu | G01R 33/4828 324/307 |
| 2012/0066895 A1* | 3/2012 | Tsuda | G01R 33/3815 165/104.19 |
| 2013/0343625 A1* | 12/2013 | Samsonov | G01R 33/5611 382/131 |
| 2014/0296696 A1 | 10/2014 | Remmele et al. | |
| 2015/0108976 A1* | 4/2015 | Fischer | G01R 33/5618 324/309 |
| 2016/0071291 A1* | 3/2016 | Samsonov | A61B 6/032 600/410 |
| 2018/0286041 A1* | 10/2018 | Hu | G06T 11/006 |

OTHER PUBLICATIONS

Communication issued in PCT Application No. PCT/US2022/019817, dated May 30, 2022, 22 pages.

International Search Report and Written Opinion Issued in Application No. PCT/US2022/019817, dated Jul. 21, 2022, 27 pages.

Assaf et al., "Non-Mono-Exponential Attenuation of Water and N-Acetyl Aspartate Signals Due to Diffusion in Brain Tissue", Journal of Magnetic Resonance, Academic Press, Mar. 1998, vol. 131, No. 1, pp. 69-85.

Burakiewicz et al., "Improved Olefinic Fat Suppression in Skeletal Muscle DTI Using a Magnitude-Based Dixon Method", Magnetic Resonance in Medicine, 2018, vol. 79, No. 1, pp. 152-159.

Mamidipalli et al., "Prosepctive comparison of longitudinal change in hepatic proton density fat fraction (PDFF) estimated by magnitude-based MRI (MRI-M) and complex-based MRI (MRI-C)", European Radiology, Springer Berlin Heidelberg, Apr. 2020, vol. 30, No. 9, pp. 5120-5129.

Ruschke et al., "Separating water and olefinic fat peaks using diffusion-weighted MRS and diffusion constraint fitting to measure vertebral bone marrow fat unsaturation", Proceedings of the International Society for Magnetic Resonance In Medicine, 23rd Annual Meeting in Exhibition, Toronto, Canada, May 30-Jun. 5, 2015, XP040666300, 1 page.

* cited by examiner

SYSTEMS AND METHODS FOR NON-INVASIVE FAT COMPOSITION MEASUREMENT IN AN ORGAN

CROSS-REFERENCE TO RELATED APPLICATIONS

This application claims the benefit of U.S. Provisional Application No. 63/159,346 filed Mar. 10, 2021 and which is hereby incorporated herein by reference in its entirety.

TECHNICAL FIELD

The present disclosure relates generally to non-invasive diagnostic systems and methods, and in particular, some implementations may relate to non-invasive diagnostic systems and methods for determining concentrations of fat and water and the diffusion coefficients of fat and water in internal organs, such as the liver.

BACKGROUND

Determining the amount of fat in organs is important to the diagnosis and treatment of diseases and other health conditions. In particular, the liver is an organ where such information is valuable, as detecting adverse changes in the fat composition of the liver may allow for early diagnose and treatment of disease leading to better health outcomes. Evaluating the fat content of the liver can assist in diagnosing and determining certain health risks, including progression of disease like fatty liver, cirrhosis, cancer, and other health conditions. Also, even absent detection of disease, the fat composition in liver can be indicative of overall health and therefore is a key measurement.

Traditional methods for assessing the fat content of the liver, such as MRI, are expensive, require a lot of space, and can be very uncomfortable for patients. Other methods may result in poor accuracy. For these reasons, monitoring of the fat composition of the liver is not a part of regular preventative medical care and diagnosis of health conditions related to the fat content of the liver are often not made until advanced disease progression. Early monitoring of changes in the liver fat composition allows for early intervention and treatment and better outcomes for patients. Accurate measurement of fat content allows for determination of treatment efficacy over time.

BRIEF SUMMARY OF THE DISCLOSURE

Systems and methods are disclosed for a non-invasive health measurement system. A non-invasive health measurement system may include an open magnet nuclear magnetic resonance ("NMR") apparatus. The NMR apparatus may obtain NMR response signals generated by atomic nuclei of substances comprising an organ. The NMR response signals may include a fat contribution signal and a water contribution signal. The system may include a processor and a memory communicably coupled to the processor. The memory may store instructions that, when executed by the processor, cause the processor to transmit radio frequency ("RF") pulses in the presence of a field gradient into the organ with the open magnet NMR apparatus. The instructions may further cause the processor to obtain the NMR response signal. The instructions may further cause the processor to separate the contributions of water and fat to the NMR response signal based on the difference in the diffusion coefficients of water and fat to determine the water and fat composition of the organ.

In an embodiment, separating the water and fat signal contributions based on the diffusion coefficients of water and fat may involve measuring the NMR signal amplitude dependence with diffusion time. Separating the water and fat signal contributions based on the diffusion coefficients of water and fat may also involve determining the amplitude and diffusion coefficients of fat and water contributions using the measured NMR signal amplitude dependence with diffusion time. In an embodiment, determining the water and fat composition of the organ may involve computing a proton density fat fraction ("PDFF") based on the determined amplitudes.

In an embodiment, the diffusion coefficient of fat may be known. Determining the water and fat composition of the organ may involve computing a PDFF by suppressing the water amplitude using a high b-value to compute the fat amplitude based on the known diffusion coefficient of fat.

In an embodiment, instructions for a non-invasive health measurement system may further cause the processor to measure a fat proton relaxation time ($T_{2f}$). Measuring a fat proton relaxation time ($T_{2f}$) may involve performing diffusion encoded NMR measurements at high b-values to suppress the water contribution and computing a fat relaxation time ($T_{2f}$) based on a single exponential fit of the diffusion encoded NMR measurements.

In an embodiment, measuring the NMR signal amplitude dependence with diffusion time may involve performing diffusion encoded NMR measurements at varying b-values, performing a double exponential fit to the NMR signal at each b-value, and computing the amplitude of the NMR signal at each b-value based on the double exponential fit.

In an embodiment, determining the amplitude and diffusion coefficients of fat and water may involve performing a double exponential fit to the total measured signal amplitude dependence with time, computing the amplitudes of the water and fat contributions based on the double exponential fit, and computing the diffusion coefficients of water and fat contributions based on the double exponential fit.

In an embodiment on the non-invasive health measurement system, the organ may be a liver. The organ may be a liver of a human patient. In an embodiment of the system, the NMR apparatus may be applied to the human patient while the human patient is lying down. In an embodiment of the system, the NMR apparatus may include a band to guide positioning of the apparatus relative to the patient. The band may be an elastomeric band.

In an embodiment of the system, accuracy of the NMR signal measurement performed by the NMR apparatus may be evaluated by applying the NMR apparatus to a patient, moving the patient laterally relative to the placement of the NMR apparatus, performing an NMR signal measurement with the NMR apparatus, and evaluating an amplitude of the signal measurement to determine the accuracy of the patient position.

In an embodiment, a non-invasive health measurement system may include an open magnet nuclear magnetic resonance ("NMR") apparatus. The NMR apparatus may obtain NMR response signals generated by atomic nuclei of substances comprising an organ. The NMR response signals may include a fat contribution signal and a water contribution signal. The system may include a processor and a memory communicably coupled to the processor. The memory may store instructions that, when executed by the processor, cause the processor to transmit radio frequency ("RF") pulses in the presence of a field gradient into the organ with the open magnet NMR apparatus. The instructions may further cause the processor to obtain the NMR response signal. The instructions may further cause the processor to separate the contributions of water and fat to the NMR response signal based on their spin-spin ("$T_2$") relaxation times to determine the water and fat composition of the organ.

In an embodiment of a non-invasive health measurement system separating the water and fat signal contributions based on their $T_2$ relaxation times may include collecting a Carr-Purcell-Meiboom-Gill ("CPMG") time series, performing a double exponential least square fit to the CPMG time series, and computing the amplitudes of the fat signal contribution and the water signal contribution based on the fit. In an embodiment, a short echo time may be used to minimize diffusion effects.

In an embodiment of a non-invasive health measurement system, separating the water and fat signal contributions based on their $T_2$ relaxation times may involve measuring the $T_2$ relaxation time for the fat protons by suppressing the water signal based on $T_1$. In another embodiment, separating the water and fat signal contributions based on their $T_2$ relaxation times may involve measuring the $T_2$ relaxation time for the fat protons by suppressing a diffusion coefficient.

In an embodiment, a non-invasive health measurement system may include an open magnet nuclear magnetic resonance ("NMR") apparatus. The NMR apparatus may obtain NMR response signals generated by atomic nuclei of substances comprising an organ. The NMR response signals may include a fat contribution signal and a water contribution signal. The system may include a processor and a memory communicably coupled to the processor. The memory may store instructions that, when executed by the processor, cause the processor to transmit radio frequency ("RF") pulses in the presence of a field gradient into the organ with the open magnet NMR apparatus. The instructions may further cause the processor to obtain the NMR response signal. The instructions may further cause the processor to separate the contributions of water and fat to the NMR response signal based on their spin-lattice ("$T_1$") relaxation times.

In an embodiment of a non-invasive health measurement system, separating the water and fat signal contributions based on their $T_1$ relaxation times may involve collecting an echo train using varying recycling delays ("rd"), the echo train being much shorter than a shortest $T_2$ value, measuring the NMR signal amplitude over the range of rd values, performing a double exponential fit of the measured signal amplitudes, determining signal amplitudes values for water and for fat, independently of $T_2$ values, based on the double exponential fit, and determining $T_1$ relaxation times for water and for fat t, independently of $T_2$ values, based on the double exponential fit.

In an embodiment of a non-invasive health measurement system, separating the water and fat signal contributions based on their $T_1$ relaxation times may involve computing $T_{1f}$ and separately computing $T_{1w}$. Computing $T_{1f}$ may involve performing NMR signal measurements at varying rd values and adding echoes, applying an NMR diffusion encoding sequence to suppress the water contribution, performing a single exponential fit to the measurements, and computing $T_{1f}$ based on the single exponential fit. Separately computing $T_{1w}$ may involve collecting a single echo with diffusion encoding at varying rd values, setting an rd value much larger than $T_{1f}$ such that as $T_{1w}$ becomes much larger than $T_{1f}$ the fat contribution becomes effectively constant, performing a single exponential fit to the measurements, and computing $T_{1w}$ based on the single exponential fit.

Other features and aspects of the disclosure will become apparent from the following detailed description, taken in conjunction with the accompanying drawings, which illustrate, by way of example, the features in accordance with various embodiments. The summary is not intended to limit the scope of the invention, which is defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

The figures are not intended to be exhaustive or to limit the invention to the precise form disclosed. It should be understood that the invention can be practiced with modification and alteration, and that the disclosed technology be limited only by the claims and the equivalents thereof.

DETAILED DESCRIPTION

Systems and methods described herein related to non-invasive diagnostic technology to measure concentrations of fat in organs. An organ of interest may be the liver. Systems and methods may be non-invasive, portable, relatively inexpensive, and accurate offering advantages over existing diagnostic technology.

A non-invasive health measurement system may include an NMR apparatus. The NMR apparatus may be an open magnet NMR apparatus. In an embodiment, the NMR apparatus may be a stand-alone medical device. The NMR apparatus may be positioned against a patient. The NMR apparatus may measure the fat composition of an organ of interest by collecting an NMR signal from a sensitive volume within the patient. The sensitive volume may correspond to a desired depth into an organ of interest in the patient, such as a liver. A stand-alone NMR apparatus may be communicably coupled to other devices to allow for processing and transmission of medical results. For example, the NMR apparatus may be communicably coupled to a user interface such as a keyboard, mouse, touch screen, a remote control device, or other interface.

An open magnet NMR apparatus may mean that a probe is unilateral or open. The probe does not need to fully surround a patient, as is the case with MRI measurements. Rather, an open magnet NMR probe may be placed in proximity and/or against an area of interest of a patient. The open magnet NMR probe may generate a sensitive volume within the patient in the area of interest either outside or inside of the boundaries of the probe.

The NMR apparatus may perform a measurement as follows. Protons and/or other atomic nuclei, such as Hydrogen's proton, spin axes within the sensitive volume may align with a magnetic field. The spin alignment of the atomic nuclei may be permuted by exciting the atomic nuclei with a radio frequency ("RF") pulse or a series of RF pulses. The RF pulses may be delivered in the sensitive volume to excite Hydrogen protons present in tissues in the sensitive volume. The spinning nucleic may be knocked off of their preferred alignment relative to the magnetic field when the RF pulse is delivered. The excited atomic nuclei may then realign to the magnetic field. As the excited atomic nuclei realign, they may emit an RF signal. This emitted RF signal is an NMR response signal. The NMR response signal may be detected by an RF receiver within an NMR apparatus. The NMR response signal may provide information about the properties and/or composition of tissues and substances within the sensitive volume.

Specifically, if the sensitive volume is an organ made up of fatty tissue, like the liver, the fat content of the liver may be determined based on NMR response signals. The signals from protons in the fat in the liver may be separated from the signals from water in the liver based on a proton NMR spectrum, diffusion coefficients, T1, or T2. Therefore a total NMR signal may be measured and may include contributions from the signals from protons in the fat and in protons in the water in the liver. Protons are abundant in water and in fat.

Figure 1:
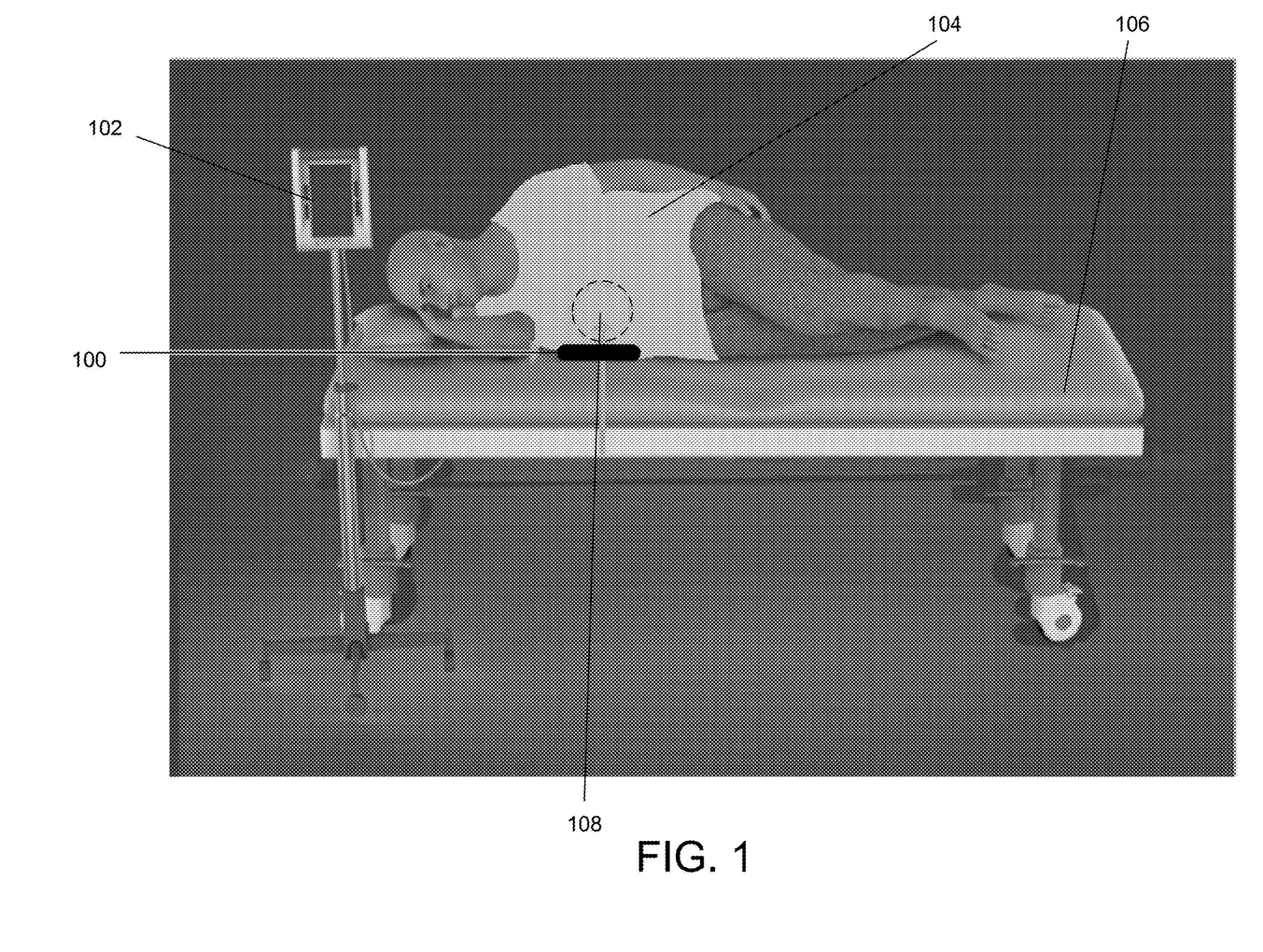
FIG. 1 is an example of an Nuclear Magnetic Resonance ("NMR") apparatus as a part of a non-invasive health measurement system in accordance with the systems and methods disclosed herein.
Figure 2:
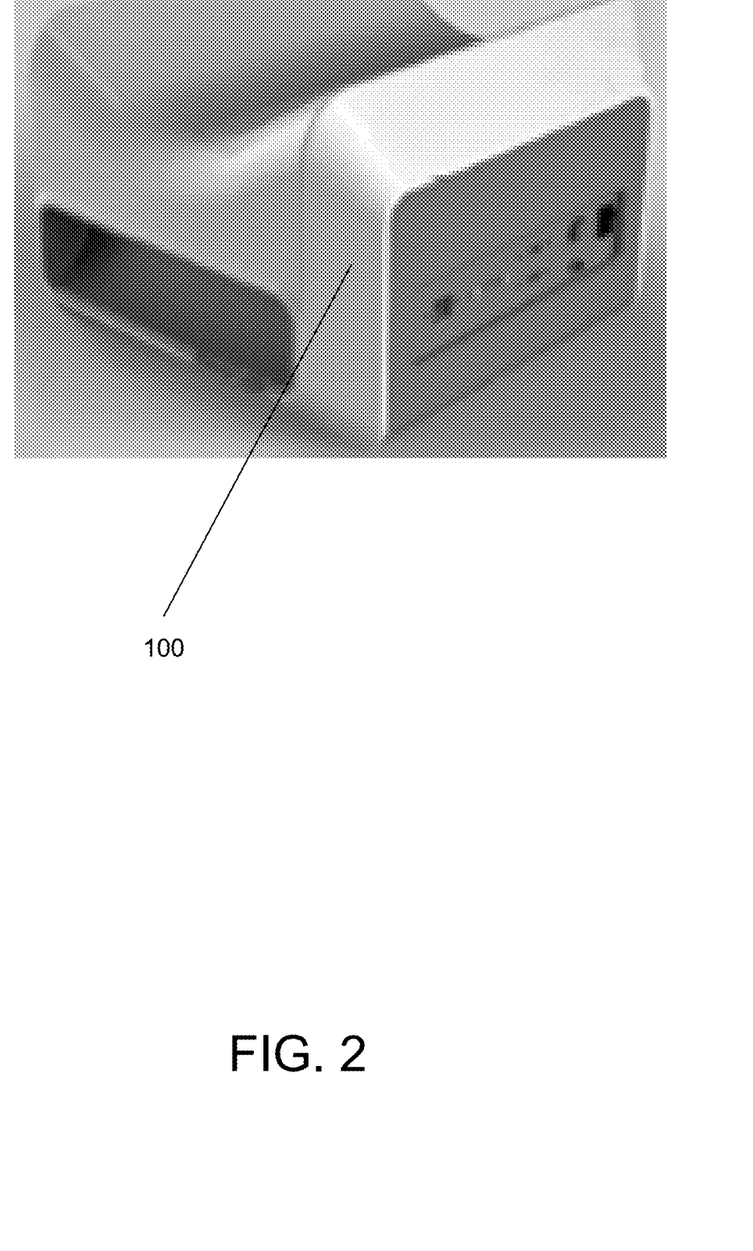
FIG. 2 is an example of a stand-alone NMR apparatus in accordance with the systems and methods disclosed herein.

FIG. 1 shows an example of an NMR apparatus 100 as part of a non-invasive health measurement system. As shown in FIG. 1, the NMR apparatus 100 is placed on a gurney 106. A human patient 104 is lying on the gurney 106 on their right side. The NMR apparatus 100 is placed below the patient's abdominal area. The NMR apparatus 100 may be aligned with the patient's sternum. The NMR apparatus 100 may include a band or strap which may be attached to the patient 104 to guide the patient positioning on the NMR apparatus. The NMR apparatus 100 may be communicably coupled to other medical instruments 102 and/or user interfaces. The NMR apparatus 100 may be configured to measure the fat composition of an organ in the patient 104 of interest by collecting an NMR signal from a sensitive volume 108 within the patient 104. The sensitive volume 108 may correspond to a desired depth into an organ of interest in the patient 104, such as the patient's liver. FIG. 2 shows an example of a stand-alone NMR apparatus 100. In an embodiment, the NMR apparatus may be integrated into a hospital bed.

In an embodiment, accuracy of the signal of the NMR device may be assessed by altering patient placement. A patient may be asked to shift laterally relative to the NMR device. For instance, a patient may be asked to move and/or moved about 2 inches toward the top of the gurney, where the patient's head is located. The NMR apparatus may then perform a test measurement of an NMR signal in the sensitive volume. If the patient is not placed correctly, the amplitude of a signal may follow a diffusion-drive response consistent with fat protons but the signal amplitude may be higher than the liver fat model prediction. Therefore, a signal amplitude higher than expected may indicate a patient is not placed correctly relative to the NMR apparatus.

A Proton Density Fat Fraction ("PDFF") may be a parameter of a fat content measurement for an organ. In an embodiment, the organ may be a liver. The PDFF may be a ratio of an amplitude of a fat proton NMR signal to a total NMR signal amplitude. The fat proton NMR signal amplitude may be proportional to a number of fat protons per unit volume. The total NMR signal amplitude may be proportional to water and fat protons per unit volume. The PDFF may be expressed as follows:

$$PDFF = \frac{100(A_{fat})}{A_{fat} + A_{water}}$$

Discrimination of water and fat signals may be achieved by separating signals responses based on different parameters. For example, different parameters may include proton relaxation times, spectroscopic responses, relaxation times, and diffusion.

In an embodiment, diffusion coefficients and relaxation times may be measured in addition to the PDFF. Diffusion and relaxation time information may correlate to droplet size and fibrosis. Fitting to collected data in accordance with the systems and methods described herein may provide new values for diffusion constants and relaxation times, which in turn may be used for other liver diagnostic applications as there may be correlation between diffusion constants and $T_1$ to stiffness and/or swelling, which may be correlated to fibrosis. Therefore, attaining diffusion constants using the methods and devices disclosed herein may provide additional clinical value.

Diffusion Based Separation Embodiment

Water and fat signals may be separated based on their diffusion coefficients. Diffusion coefficients for water and fat may be significantly different which may make this method effective to separate water and fat signals. It may be possible to suppress water signals while observing fat signals. The diffusion coefficient for water may be on the order of ten times higher than the diffusion coefficient of fat. Therefore, a clear separation of the NMR signals from the water protons and fat protons may be achieved. The signals may be differentiated by performing measurements in the presence of a magnetic field gradient. For example, a Carr-Purcell-Meiboom-Gill ("CPMG") pulse sequence with different inter pulse spacing may be used. A CPMG sequence with a diffusion encoding preparation stage may also be used. Phase cycling of RF pulses and signal channels may be performed to eliminate unwanted spurious signals.

Signal amplitudes for varying diffusion encoding times can be modeled considering diffusion coefficients for water and fat protons. Signal decay in a Hahn echo or CPMG sequence in the presence of a field gradient may depend on inter-echo spacing. A higher diffusion coefficient may positively correlate with a faster decay. Varying inter-echo spacings may allow for computation of the contributions of water and fat, respectively, to the total signal. Diffusion encoding may also be achieved by applying preparation pulses followed by a multi-echo sequence. A multi-echo sequence may be a CPMG sequence. Sensitivity may be boosted if a CPMG sequence is used after the preparation pulses.

NMR signal amplitude may decrease as a function of encoding time. A b-value may be used to scale a time series with a static field gradient, G. The b-value may be expressed as follows:

$$b = \gamma^2 G^2 \tau 3/12$$

where $\gamma$ is the gyromagnetic ratio of proton spins, having a value of 267,520,000 rad/(sT)), and G=1.875 T/m in an embodiment of a device in accordance with the systems and methods disclosed herein.

For pulse sequences, the signal amplitude of the first echo may be a function of the initial pulse separation. Then, each echo in the CPMG section may decay exponentially. For a signal generated by fat and water proton signals, decay may be represented by a double exponential decay.

To increase signal to noise ratio ("SNR"), a diffusion encoding sequence may be repeated and the signal may be added. For white Gaussian noise, when repetition is performed after the spins are fully polarized, the SNR increases as the square root of the number of repetitions.

For a recycling delay, or time between sequences, rd, the NMR signal amplitude at a time t along the CPMG time series may be expressed for a diffusion encoding time, $\tau$. The b-value ($b = \gamma^2 G^2 \tau 3/12$), discussed above, depends on the diffusion encoding time, $\tau$. The NMR signal amplitude may be expressed as follows:

$$A(b,t) = A_{water}(b=0, t=0)e^{-D_w b}e^{-t/T_{2w}}(1 - e^{-rd/T_{1w}}) + A_{fat}(b=0, t=0)e^{-D_f b}e^{-t/T_{2f}}(1 - e^{-rd/T_{1f}})$$

$A_{water}(b=0, t=0)$ is the signal amplitude of the first echo (t=0) from water protons when there is no diffusion encoding (b=0). The signal amplitude is proportional to the concentration of protons in water. The fat proton signal amplitudes can be expressed similarly. The PDFF may then be given as:

$$PDFF = 100 \frac{A_{fat}(b=0, t=0)}{A_{fat}(b=0, t=0) + A_{water}(b=0, t=0)}$$

For full polarization prior to repeating the pulse sequence, the amplitude may be given by the following expression, assuming that rd is much greater than $T_{1f}$ and $T_{1w}$:

$$A(b,t) = A_{water}(b=0,t=0)e^{-D_w b}e^{-t/T_{2w}} + A_{fat}(b=0,t=0)e^{-D_f b}e^{-t/T_{2f}}$$

$T_1$ correction may not be necessary when long repetition delays are used, as the amplitude does not depend on $T_1$ values for water or fat protons in this embodiment. The amplitude at t=0 may be determined by identifying the zero crossing in the amplitude time series of the echo train. Determining the amplitude at t=0 may depend on $T_{2f}$ and $T_{2w}$. Computing the amplitude at t=0 may be simplified by using echo train durations much shorted than $T_{2f}$ and $T_{2w}$ and then adding or averaging all echoes to increase sensitivity. This way, the amplitude at t=0 may be determine independent of $T_{2f}$ and $T_{2w}$. Additionally, if rd is assumed to be much greater than $T_{1f}$ and $T_{1w}$, as stated above, diffusion encoded signal may also be attained independently of $T_{1f}$ and $T_{1w}$. Therefore, if appropriate time parameters are used during signal acquisition, the diffusion encoded signal may be determined independently of both $T_{2f}$ and $T_{2w}$ and $T_{1f}$ and $T_{1w}$.

For long diffusion encoding times, only the fat signal may be observed. The amplitude, depending only on the fat signal given the high b-value due to the long diffusion encoding time, may be given by the following expression:

$$A(b,t) = A_{fat}(b=0, t=0)e^{-D_f b}e^{-t/T_{2f}}(1 - e^{-rd/T_{1f}})$$

With full polarization, when the b-value is high and when rd is assumed to be much greater than $T_{1f}$, the amplitude may be given by the following expression:

$$A(b,t) = A_{fat}(b=0, t=0)e^{-t/T_{2f}}(1 - e^{-rd/T_{1f}})$$

Therefore, as given above, a single exponential decay may be observed from the fat signals. This signal exponential decay function may facilitate easy measurement of $T_{2f}$. A single exponential fit to the CPMG time series may facilitate determination of both $T_{2f}$ and the amplitude of the diffusion-encoded fat signal.

The diffusion-encoded NMR signals may be collected at various encoding times, $\tau$, which result in varying b-values. This may allow computation of the PDFF, discussed above, and the diffusion coefficients for water and fat. The CPMG time series may be expressed as a double exponential decay function, driven by $T_{2f}$ and $T_{2w}$, for each b-value. The $T_1$ values for water and fat protons may not be known. However, assuming and/or setting a long rd may avoid the need to perform $T_1$ corrections, as discussed above.

Figure 3:
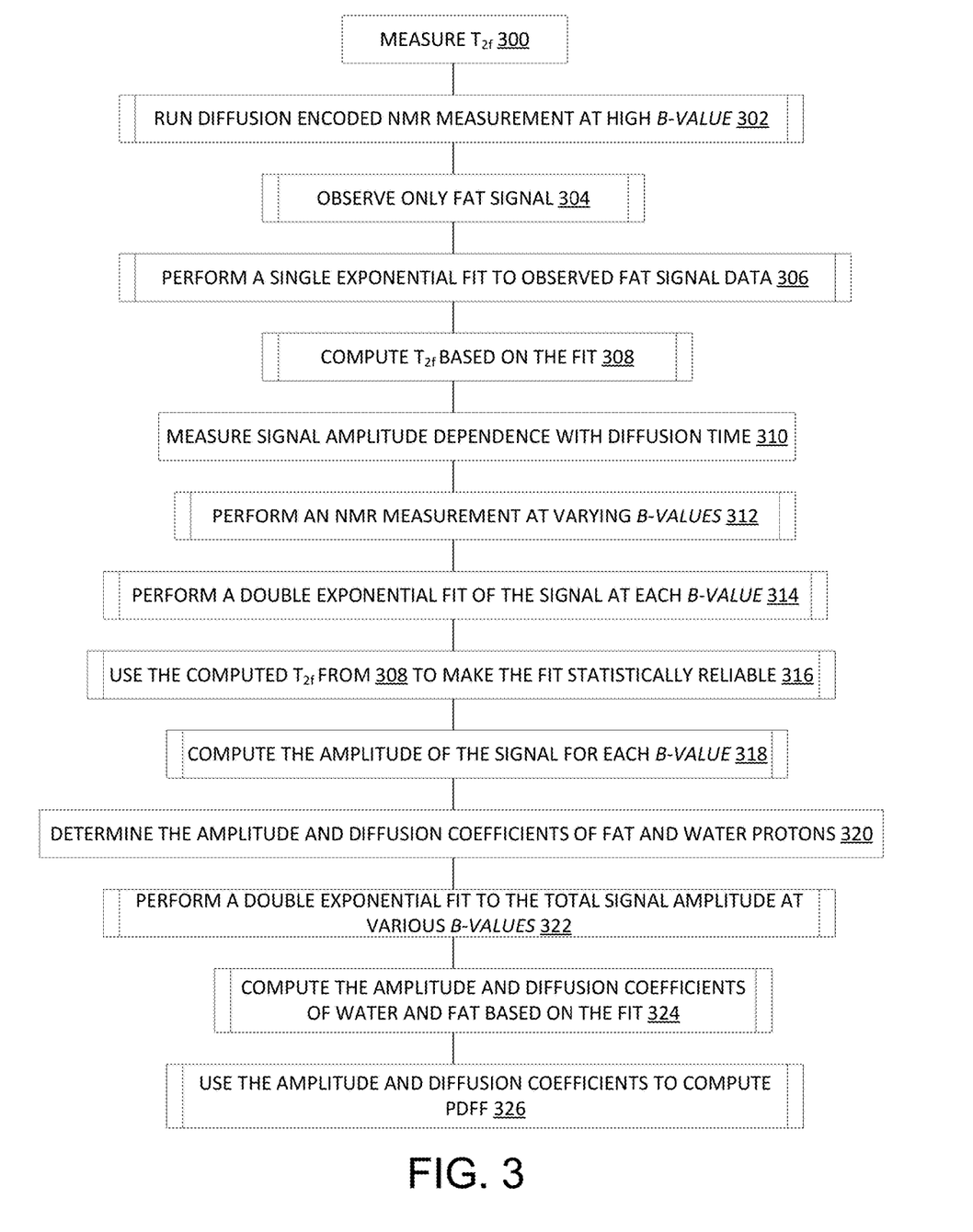
FIG. 3 is an example of a flow diagram illustrating how the PDFF and diffusion coefficients may be computed in accordance with embodiments of the systems and methods disclosed herein.

The PDFF and diffusion coefficients may be computed, consistent with the above described embodiments, using the following method. FIG. 3 shows an example of a flow diagram illustrating how the PDFF and diffusion coefficients may be computed based on diffusion contrast. As a first operation 300, $T_{2f}$ may be measured. As a first sub-operation 302 to the first operation 300, to measure $T_{2f}$, a diffusion-encoded NMR measurement may be run at a high b-value. As a second sub-operation 304 to the first operation 300, this configuration may enable observation of only the fat signal, as discussed above. As a third sub-operation 306 to the first operation 300, a single exponential fit to the data may be performed. As a fourth sub-operation 308 to the first operation 300, the fat proton relaxation time ($T_{2f}$) may then be computed based on the single exponential fit. In an embodiment, the SNR may be high and the signals from fat and water may already be effectively singled out for a CPMG time series for each encoding time. Therefore, if the SNR is high, this operation may not be necessary.

As a second operation 310, the signal amplitude dependence with diffusion time may be measured. As a first sub-operation 312 to the second operation 310, an NMR measurement may be run at various b-values. As a second sub-operation 314 to the second operation 310, a double exponential fit of the signal may be performed at each b-value. As a third-sub-operation 316 to the second operation 310, the $T_{2f}$ computed from the fourth sub-operation 308 to the first operation 300 may be used to make the fit statistically reliable. As a fourth sub-operation 318 to the second operation 310, the amplitude of the signal at each b-value (t=0) may be computed.

As a third operation 320, the amplitude and diffusion coefficients of fat and water protons may be determined. As a first sub-operation 322 to the third operation 320, a double exponential fit to the total signal amplitude may be performed. As a second sub-operation 324 to the third operation 320, the amplitude and diffusion coefficients of water and fat protons may be computed based on the double exponential fit. As a third sub-operation 326 to the third operation 320, the amplitudes and coefficients may be used to compute the PDFF.

In an embodiment, during operation of the NMR apparatus, an operator may instruct a patient to breath in, breath out, and hold while the NMR apparatus measures an NMR signal within the sensitive volume of the patient. The patient may hold their breath for 5 to 15 seconds for each b-value for which an NMR measurement is desired.

In an embodiment, if the diffusion coefficient of fat is known, the PDFF may be evaluated by suppressing the water signal with a high b value in a diffusion-encoded signal to attain $A_{fat}$ (b, t=0) using:

$$A_{fat}(b=0,t=0)=A(b,t)e^{D_f b}e^{t/T_{2f}}$$

If the echoes are added over a time much shorter that $T_{2f}$, $$A_{fat}(b=0,t=0)=A(b,t)e^{D_f b}$$

This simplifies the measurement of the fat signal response and therefore a fast PDFF reading may be performed. If the total signal is assumed to be constant from patient to patient, PDFF may be measured using a single measurement at high b value to determine the fat signal and the known total signal response.

$T_2$ Based Separation Embodiment

Figure 4:
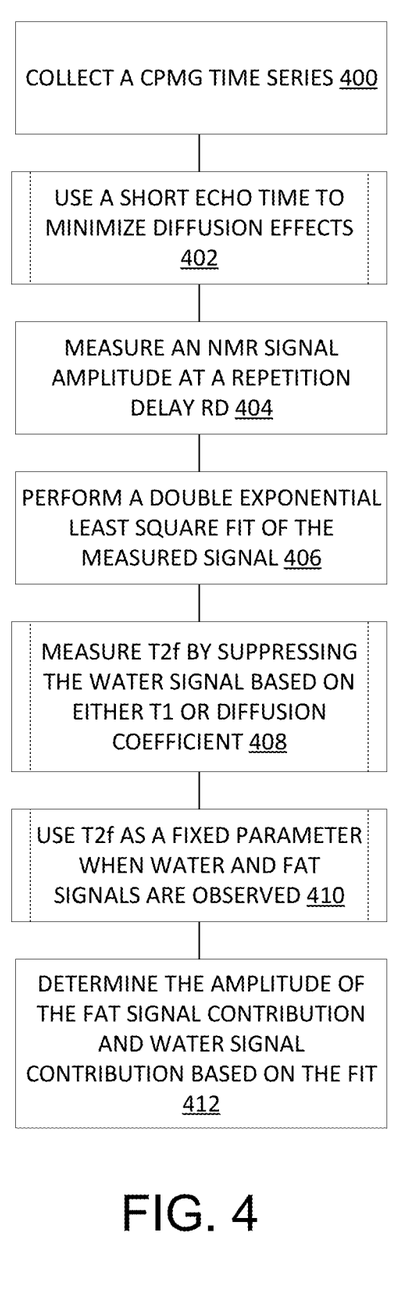
FIG. 4 is an example of a flow diagram illustrating how water and fat signals may be separated in accordance with embodiments of the systems and methods disclosed herein.

Water and fat signals may also be separated based on their spin-spin relaxation times ($T_2$), or $T_{2eff}$, a time constant in a multi-echo pulse sequence. FIG. 4 shows an example of a flow diagram illustrating how water and fat signals may be separated based on their $T_2$. As a first operation 400, a CPMG time series may be collected. As above for the diffusion based separation embodiment, phase cycling of RF pulses and signal channels may be performed to eliminate unwanted spurious signals.

As a sub-operation 402 to the first operation 400, a short echo time may be used to minimize diffusion effects during an echo train. A longer echo spacing may reduce the signal of water more than the signal from fat which may result in an inaccurate PDFF computation. As a third operation 404, an NMR signal may be measured at a repetition delay, rd. An NMR signal using a repetition delay, rd, may be given by the below expression:

$$A(t)=A_{water}e^{-t/T_{2w}}(1-e^{-rd/T_{1w}})+A_{fat}e^{-t/T_{2f}}(1-e^{-rd/T_{1f}})$$

As a fourth operation 406, a double exponential least square fit may be performed to single out the signal contributions from fat and water. As a fifth operation 412, the amplitudes of signals from fat and water may be computed using a double exponential fit to the echo amplitude in the CPMG time series. The $A_{water}$ and $A_{fat}$ yielded by the double exponential fit may be used to compute the PDFF. As rd becomes much larger than $T_{1w}$ and $T_{1f}$, the expression may be simplified as follows:

$$A(t)=A_{water}e^{-t/T_{2w}}+A_{fat}e^{-t/T_{2f}}$$

This method may quantify the contributions of water and fat protons to the NMR signal. To assist in achieving separation of the two signals, as a first sub-operation 408 to the fourth operation 406, $T_{2f}$ can be measured by suppressing the water signal based on $T_1$, using fast repetition, or based on the diffusion coefficient, using a diffusion encoding sequence or large echo spacing. As a second sub-operation 410 to the fourth operation 406, $T_{2f}$ can then be used as a fixed parameter when the water and fat signals are observed.

$T_1$ Based Separation Embodiment

Figure 5:
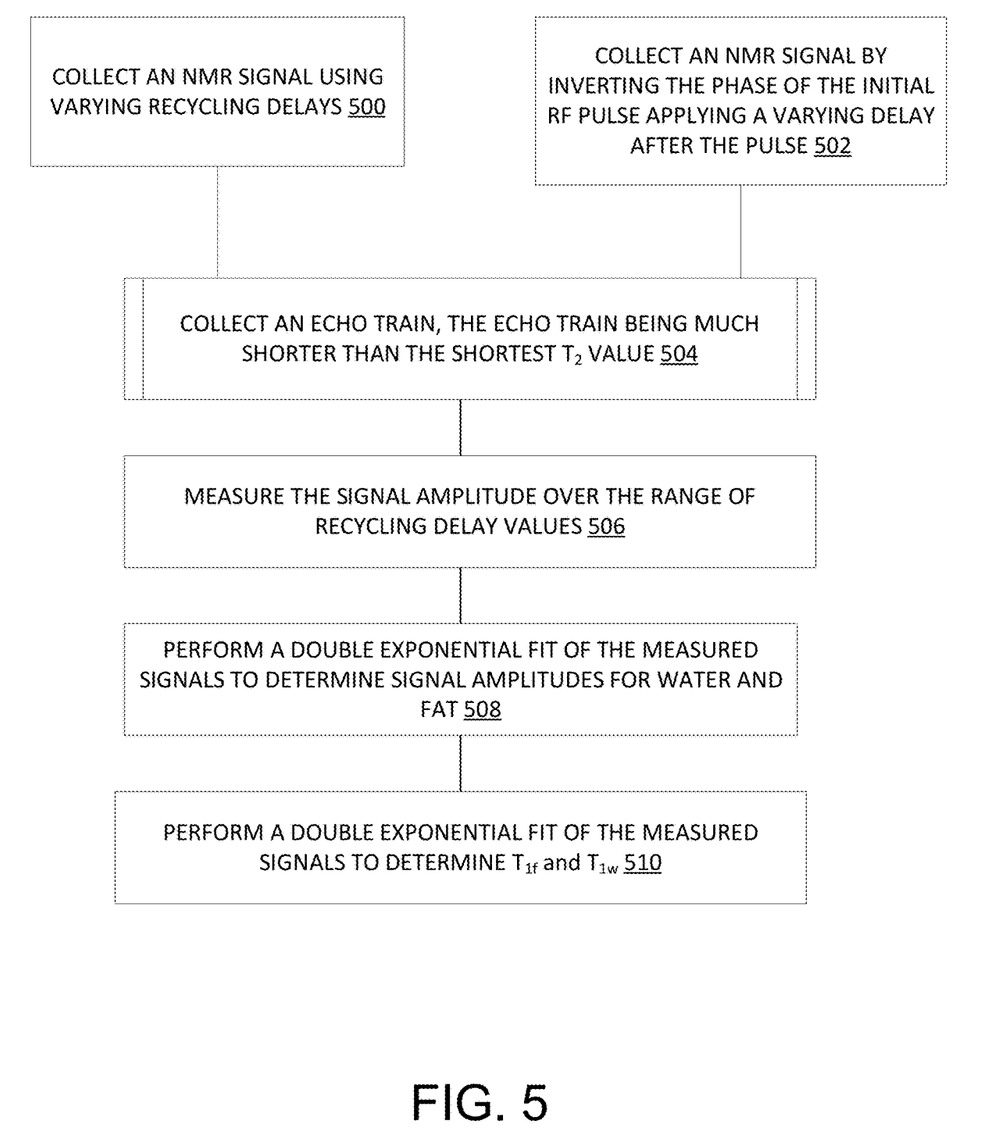
FIG. 5 is an example of a flow diagram illustrating how water and fat signals may be separated and how $T_1$ of water and fat may be measured in accordance with embodiments of the systems and methods disclosed herein.

Water and fat signals may also be separated based on spin-lattice relaxation time ($T_1$) differences. The $T_1$ of water ($T_{1w}$) may be roughly four times longer than the $T_1$ of fat ($T_{1f}$), which may make separation on this basis feasible. $T_1$ tests may be time consuming, though. FIG. 5 is an example of a flow diagram illustrating how water and fat signals may be separated based on $T_1$. As a first operation 500, differentiation of fat and water proton signals may be achieved by signal saturation. In the first operation 500, an NMR signal may be collected using varying recycling delays. In an alternative first operation 502, differentiation of fat and water proton signals may also be achieved using inverse recovery methods. In the alternative first operation 502, an NMR signal may be collected by inverting the phase of the initial RF pulse and applying a varying delay after the pulse.

Because the polarization time of the fat and water signals are different, a double exponential analysis of the response may be used to separate the contributions of water and fat to the signal. In an embodiment, a single echo sequence may be repeated. An NMR signal with a repetition time, rd, may be expressed as follows, if the first echo is discarded:

$$A(rd)=A_{water}(1-e^{-rd/T_{1w}})+A_{fat}(1-e^{-rd/T_{1f}})$$

As a second operation 506, the signal amplitude may be measured over a series of rd values. Then, as a third operation 508, a double exponential fit of the data may be used to generate fat and water signal amplitudes. As a fourth operation 510, the double exponential fit may also be used to determine both $T_{1w}$ and $T_{1f}$. The computed $A_{water}$ and $A_{fat}$ may then be used to compute the PDFF. See, supra at para. [0037].

To increase sensitivity, as a sub-operation 504 to the first operation 500 or to the alternative first operation 502, an echo train may be collected instead of a single echo. The signal processing in this instance may consider that the time series during the echo train is driven by the $T_2$ of water and fat protons. If the echo train is much shorter than the shortest $T_2$ value, echoes may be added to increase sensitivity, with minimal $T_2$ bias. In this way, sensitivity may be increased over a single echo test, without having to perform a fitting to a multi-echo time series.

Figure 6A:
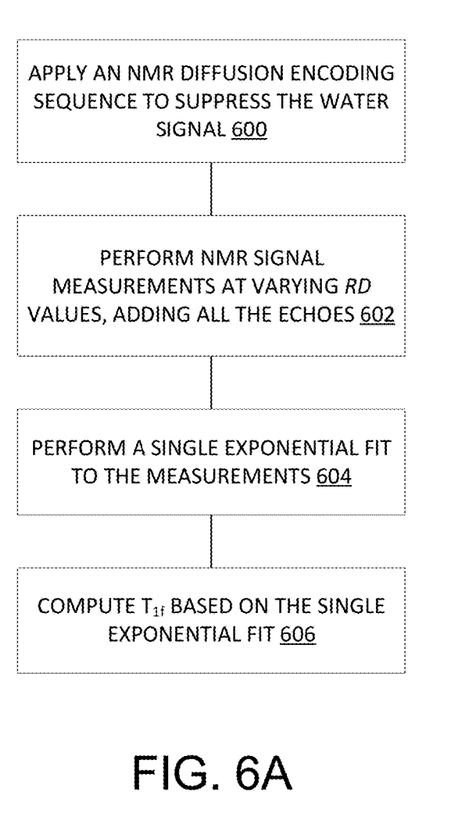
FIG. 6A is an example of a flow diagram illustrating an embodiment in which $T_{1f}$ may be computed using an NMR diffusion encoding sequence to suppress the water signal and measure the fat signal alone in accordance with embodiments of the systems and methods disclosed herein.

In other embodiments, $T_1$ values for water and fat may also be measured separately. FIG. 6A shows an example of a flow diagram illustrating an embodiment in which $T_{1f}$ may be computed using an NMR diffusion encoding sequence to suppress the water signal and measure the fat signal alone. This may simplify the analysis because there will only be a single-exponential time series. An effective method to run this reading and process the data may be to, as a first operation 600, an NMR diffusion encoding sequence may be applied to suppress the water signal. As a second operation 602, perform measurements with varying rd values, adding all the echoes. As a third operation 604, a single exponential fitting to the resulting data may be performed. As a fourth operation 606, $T_{1f}$ may be computed based on the single exponential fitting. This $T_1$ value may be used as a fix parameter on a double exponential decay when there is no diffusion encoding—aiding the separation of water and fat signals.

Figure 6B:
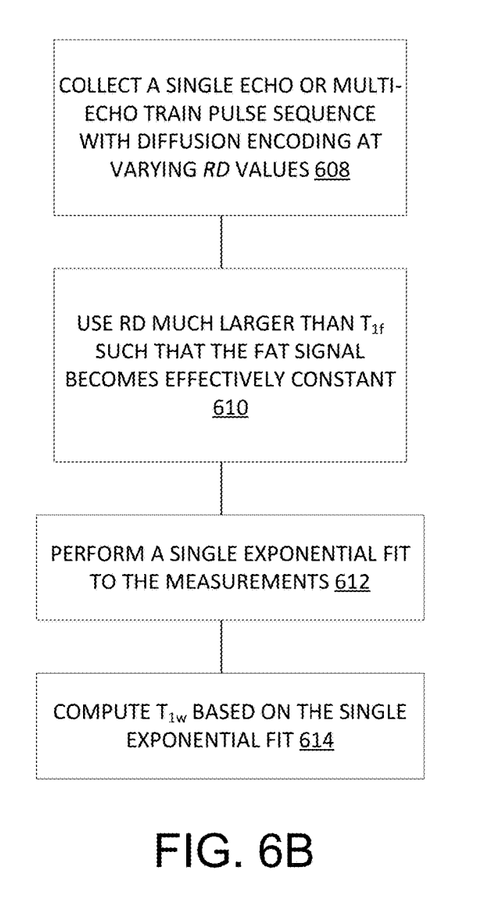
FIG. 6B shows an example of a flow diagram illustrating an embodiment in which $T_{1w}$ may be computed.

FIG. 6B shows an example of a flow diagram illustrating an embodiment in which $T_{1w}$ may be computed. As a first operation 608, a single echo or multi-echo train pulse sequence with diffusion encoding, for example CPMG, with varying rd values may be collected. As a second operation 610, as $T_{1w}$ becomes much larger than $T_{1f}$ and using an rd much larger than $T_{1f}$ the fat signal may become effectively constant which may result in the signal recovery becoming dominated by the water signal. Therefore, as a third operation 612, a single exponential function may be applied to approximate the signal recovery when rd is much larger than $T_{1f}$. As a fourth operation 614, $T_{1w}$ may be computed based on the single exponential fit.

J-Coupling Based Separation Embodiment

J-coupling may also be used to separate signals. A pulse separation may be applied that may cause the water signals to be out of phase while the fat signals refocus.

Figure 7:
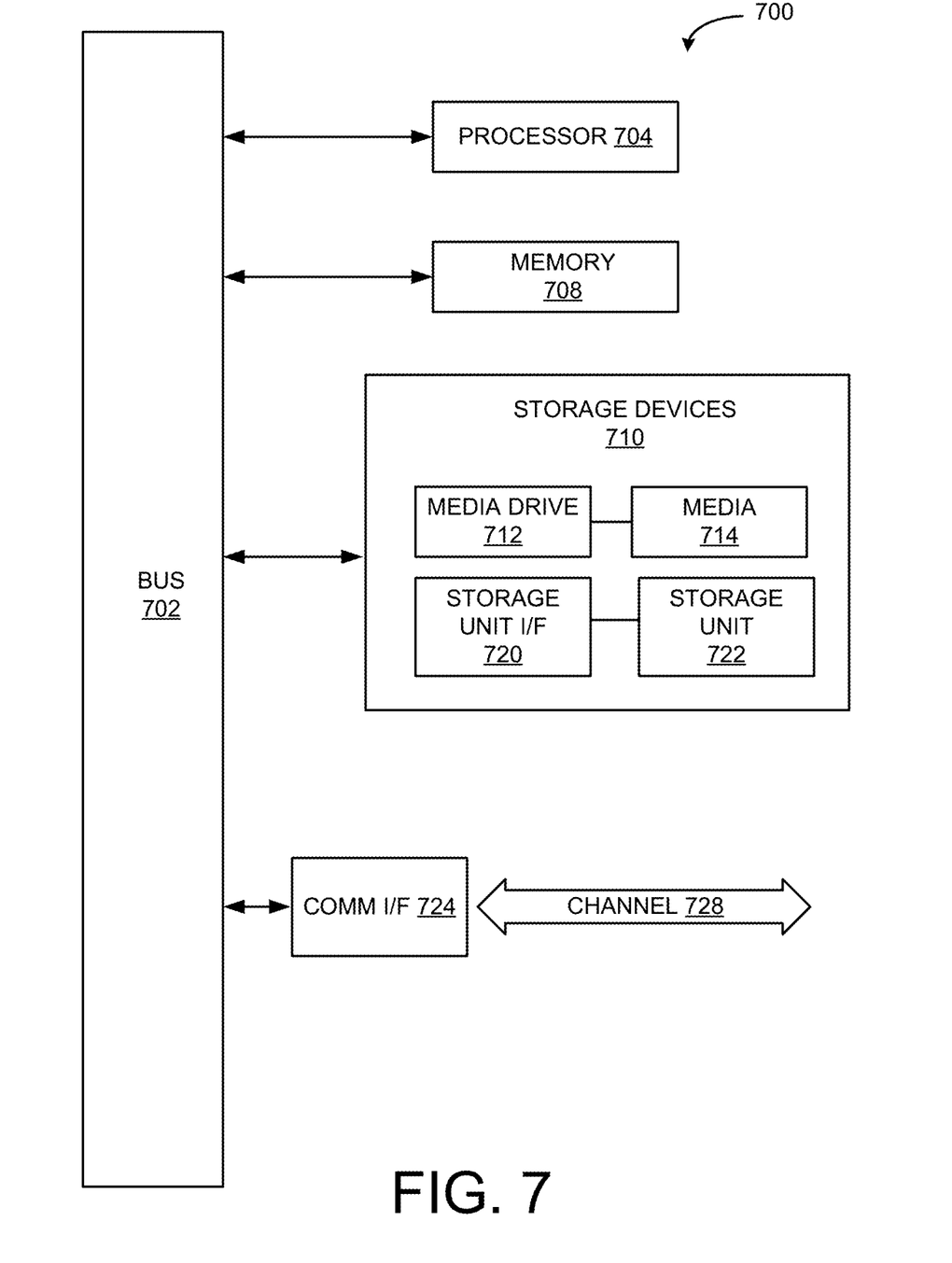
FIG. 7 is an example computing component that may be used to implement various features of embodiments described in the present disclosure.

Example Integration with Computing Components

Where components are implemented in whole or in part using software, these software elements can be implemented to operate with a computing or processing component capable of carrying out the functionality described with respect thereto. One such example computing component is shown in FIG. 7. Various embodiments are described in terms of this example-computing component 700. After reading this description, it will become apparent to a person skilled in the relevant art how to implement the application using other computing components or architectures.

Referring now to FIG. 7, computing component 700 may represent, for example, computing or processing capabilities found within a self-adjusting display, desktop, laptop, notebook, and tablet computers. They may be found in hand-held computing devices (tablets, PDA's, smart phones, cell phones, palmtops, etc.). They may be found in workstations or other devices with displays, servers, or any other type of special-purpose or general-purpose computing devices as may be desirable or appropriate for a given application or environment. They may be found in smart medical devices. Computing component 700 might also represent computing capabilities embedded within or otherwise available to a given device. For example, a computing component might be found in other electronic devices such as, for example, portable computing devices, smart medical devices, and other electronic devices that might include some form of processing capability.

Computing component 700 might include, for example, one or more processors, controllers, control components, or other processing devices. This can include a processor, and/or any one or more of the components making up a user device, a user system, and/or a non-decrypting cloud service. Processor 704 might be implemented using a general-purpose or special-purpose processing engine such as, for example, a microprocessor, controller, or other control logic. Processor 704 may be connected to a bus 702. However, any communication medium can be used to facilitate interaction with other components of computing component 700 or to communicate externally.

Computing component 700 might also include one or more memory components, simply referred to herein as main memory 708. For example, random access memory (RAM) or other dynamic memory, might be used for storing information and instructions to be executed by processor 704. Main memory 708 might also be used for storing temporary variables or other intermediate information during execution of instructions to be executed by processor 704. Computing component 700 might likewise include a read only memory ("ROM") or other static storage device coupled to bus 702 for storing static information and instructions for processor 704.

The computing component 700 might also include one or more various forms of information storage mechanism 710, which might include, for example, a media drive 712 and a storage unit interface 720. The media drive 712 might include a drive or other mechanism to support fixed or removable storage media 714. For example, a hard disk drive, a solid-state drive, a magnetic tape drive, an optical drive, a compact disc (CD) or digital video disc (DVD) drive (R or RW), or other removable or fixed media drive might be provided. Storage media 714 might include, for example, a hard disk, an integrated circuit assembly, magnetic tape, cartridge, optical disk, a CD or DVD. Storage media 714 may be any other fixed or removable medium that is read by, written to or accessed by media drive 712. As these examples illustrate, the storage media 714 can include a computer usable storage medium having stored therein computer software or data.

In alternative embodiments, information storage mechanism 710 might include other similar instrumentalities for allowing computer programs or other instructions or data to be loaded into computing component 700. Such instrumentalities might include, for example, a fixed or removable storage unit 722 and an interface 720. Examples of such storage units 722 and interfaces 720 can include a program cartridge and cartridge interface, a removable memory (for example, a flash memory or other removable memory component) and memory slot. Other examples may include a PCMCIA slot and card, and other fixed or removable storage units 722 and interfaces 720 that allow software and data to be transferred from storage unit 722 to computing component 700.

Computing component 700 might also include a communications interface 724. Communications interface 724 might be used to allow software and data to be transferred between computing component 700 and external devices. Examples of communications interface 724 might include a modem or softmodem, a network interface (such as Ethernet, network interface card, IEEE 802.XX or other interface). Other examples include a communications port (such as for example, a USB port, IR port, RS232 port Bluetooth® interface, or other port), or other communications interface. Software/data transferred via communications interface 724 may be carried on signals, which can be electronic, electromagnetic (which includes optical) or other signals capable of being exchanged by a given communications interface 724. These signals might be provided to communications interface 724 via a channel 728. Channel 728 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media. Such media may be, e.g., memory 708, storage unit 720, media 714, and channel 728. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing component 700 to perform features or functions of the present application as discussed herein.

In an embodiment, computing components may be integrated with, communicably coupled to, or otherwise form part of a laboratory system. For example, computing components may be communicably coupled to medical and/or laboratory instrumentation. In another example computing components may be part of a medical workstation. The medical workstation may be set up as a mobile cart. The medical workstation may also be stationary. A standalone NMR apparatus may be communicably coupled to the medical workstation. AN NMR apparatus integrated into a patient bed may also be communicably coupled to a medical workstation.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A non-invasive health measurement system comprising:
   an open magnet Nuclear Magnetic Resonance ("NMR") apparatus to obtain NMR response signals generated by atomic nuclei of substances comprising an organ, the NMR response signals comprising a fat contribution signal and a water contribution signal;
   a processor; and
   a memory communicably coupled to the processor and storing instructions that, when executed by the processor, cause the processor to:
      transmit radio frequency ("RF") pulses in a presence of a field gradient into the organ with the open magnet NMR apparatus;
      obtain the NMR response signals; and
      separate contributions of water and fat to the NMR response signals based on a difference in diffusion coefficients of water and fat to determine a water composition and a fat composition of the organ by measuring the NMR response signals' amplitude dependence with diffusion time and determining amplitude and diffusion coefficients of fat and water contributions using the measured amplitude dependence with diffusion time.

2. The system of claim 1 wherein separating the water and fat signal contributions based on the diffusion coefficients of water and fat further comprises computing a proton density fat fraction ("PDFF") based on the determined amplitudes.

3. The system of claim 1 wherein the diffusion coefficient of fat is known and wherein separating the water and fat signal contributions based on the diffusion coefficients of water and fat further comprises computing a PDFF by suppressing water amplitude using a high b-value to compute fat amplitude based on the known diffusion coefficient of fat.

4. The system of claim 1 wherein the processor is further caused to measure a fat proton relaxation time ($T_{2f}$).

5. The system of claim 4 wherein measuring a fat proton relaxation time ($T_{2f}$) comprises:
performing diffusion encoded NMR measurements at high b-values to suppress the water contribution; and
computing a fat relaxation time ($T_{2f}$) based on a single exponential fit of the diffusion encoded NMR measurements.

6. The system of claim 1 wherein measuring the NMR signal amplitude dependence with diffusion time:
performing diffusion encoded NMR measurements at varying b-values;
performing a double exponential fit to the NMR signal at each b-value; and
computing the amplitude of the NMR signal at each b-value based on the double exponential fit.

7. The system of claim 1 wherein determining the amplitude and diffusion coefficients of fat and water comprises:
performing a double exponential fit to the total measured signal amplitude dependence with diffusion time;
computing the amplitudes of the water and fat contributions based on the double exponential fit; and
computing the diffusion coefficients of water and fat based on the double exponential fit.

8. The system of claim 1 wherein the organ is a liver.

9. The system of claim 8 wherein the organ is a liver of a human patient.

10. The system of claim 8 wherein the NMR apparatus is applied to a human patient while the human patient is lying down.

11. The system of claim 1 wherein the NMR apparatus is applied to a patient and wherein the NMR apparatus comprises a band to guide positioning of the patient.

12. The system of claim 11 wherein the band comprises an elastomeric band.

13. The system of claim 1 wherein accuracy of the NMR signal measurement performed by the NMR apparatus is evaluated by:
applying the NMR apparatus to a patient;
moving the patient laterally relative to a placement of the NMR apparatus;
performing an NMR signal measurement with the NMR apparatus; and
evaluating an amplitude of the signal measurement to determine the accuracy of the patient's position.

14. A method for using an open magnet Nuclear Magnetic Resonance ("NMR") apparatus to obtain NMR response signals generated by atomic nuclei of substances comprising an organ, the NMR response signals comprising a fat contribution signal and a water contribution signal, the method comprising:
transmitting radio frequency ("RF") pulses in a presence of a field gradient into the organ with the open magnet NMR apparatus;
obtaining the NMR response signals; and
measuring the NMR response signals' amplitude dependence with diffusion time;
determining amplitude and diffusion coefficients of fat and water contributions using the measured amplitude dependence with diffusion time;
computing a proton density fat fraction ("PDFF") based on the determined amplitudes; and
determining water and fat composition of the organ based on the PDFF.

15. The method of claim 14, wherein the diffusion coefficient of fat is known and wherein separating water and fat signal contributions based on the diffusion coefficients of water and fat further comprises computing a PDFF by suppressing the water amplitude using a high b-value to compute the fat amplitude based on the known diffusion coefficient of fat.

16. The method of claim 14, further comprising measuring a fat proton relaxation time ($T_{2f}$).

17. The method of claim 16, wherein measuring the fat proton relaxation time ($T_{2f}$) comprises:
performing diffusion encoded NMR measurements at high b-values to suppress the water contribution; and
computing a fat relaxation time ($T_{2f}$) based on a single exponential fit of the diffusion encoded NMR measurements.

18. The method of claim 14, wherein measuring the NMR signal amplitude dependence with diffusion time comprises:
performing diffusion encoded NMR measurements at varying b-values;
performing a double exponential fit to the NMR signal at each b-value; and
computing the amplitude of the NMR signal at each b-value based on the double exponential fit.

19. The method of claim 14, wherein determining the amplitude and diffusion coefficients of fat and water comprises:
performing a double exponential fit to the total measured signal amplitude dependence with diffusion time;
computing the amplitudes of the water and fat contributions based on the double exponential fit; and
computing the diffusion coefficients of water and fat based on the double exponential fit.

20. The method of claim 14, wherein accuracy of the NMR signal measurement is evaluated by:
applying the NMR apparatus to a patient;
moving the patient laterally relative to a placement of the NMR apparatus;
performing an NMR signal measurement with the NMR apparatus; and
evaluating an amplitude of the signal measurement to determine the accuracy of the patient's position.

* * * * *